(12) United States Patent
Schechter

(10) Patent No.: US 9,868,495 B2
(45) Date of Patent: Jan. 16, 2018

(54) CONTROLLABLE WATER FLOATATION GARMENT

(71) Applicant: SAFE SWIM LTD., Zipori (IL)

(72) Inventor: Amir Schechter, Kadima (IL)

(73) Assignee: SAFE SWIM LTD., Zipori (IL)

( * ) Notice: Subject to any disclaimer, the term of this patent is extended or adjusted under 35 U.S.C. 154(b) by 0 days.

(21) Appl. No.: 15/103,339

(22) PCT Filed: Dec. 11, 2014

(86) PCT No.: PCT/IL2014/051083
§ 371 (c)(1),
(2) Date: Jun. 10, 2016

(87) PCT Pub. No.: WO2015/087330
PCT Pub. Date: Jun. 18, 2015

(65) Prior Publication Data
US 2016/0355245 A1    Dec. 8, 2016

Related U.S. Application Data

(60) Provisional application No. 61/914,465, filed on Dec. 11, 2013.

(51) Int. Cl.
| | |
|---|---|
| *B63C 11/08* | (2006.01) |
| *B63C 9/00* | (2006.01) |
| *B63C 9/105* | (2006.01) |
| *A61B 5/11* | (2006.01) |
| *A61B 5/00* | (2006.01) |

(Continued)

(52) U.S. Cl.
CPC ............ *B63C 11/08* (2013.01); *A61B 5/0806* (2013.01); *A61B 5/1123* (2013.01); *A61B 5/6805* (2013.01); *B63C 9/00* (2013.01); *B63C 9/1055* (2013.01); *B63C 9/1255* (2013.01); *B63C 11/02* (2013.01); *B63C 11/26* (2013.01); *G08B 21/088* (2013.01); *A61B 5/08* (2013.01); *A61B 2562/0219* (2013.01);

(Continued)

(58) Field of Classification Search
CPC .... B63C 9/00; B63C 9/08; B63C 9/18; B63C 9/20; B63C 9/21; B63C 9/1055; B63C 9/0005; B63C 11/08; A61B 5/08
USPC ................................... 441/89, 107
See application file for complete search history.

(56) References Cited

U.S. PATENT DOCUMENTS

| | | |
|---|---|---|
| 6,064,309 A | 5/2000 | Sellers et al. |
| 7,699,679 B2 | 4/2010 | Lahyani |

(Continued)

FOREIGN PATENT DOCUMENTS

| | | |
|---|---|---|
| CN | 202593830 U | 12/2012 |
| EP | 1 961 654 | 8/2008 |
| WO | 2010/125529 | 11/2010 |

OTHER PUBLICATIONS

International Search Report for International Application PCT/IL2014/051083, dated May 18, 2015.
IPRP for PCT/IL2014/051083, dated Jan. 6, 2016.

*Primary Examiner* — Lars A Olson
(74) *Attorney, Agent, or Firm* — The Law Office of Joseph L. Felber

(57) ABSTRACT

The present invention relates to a water floatation garment, and in particular, to such a swimming garment incorporating a fillable bladder and electronics provided to identify emergency situation such as drowning based on sensed data that causing the garment to trigger the fillable bladder to inflate allowing a user to float to surface therein preventing a drowning.

20 Claims, 7 Drawing Sheets

(51) Int. Cl.

| | |
|---|---|
| *B63C 9/125* | (2006.01) |
| *B63C 11/02* | (2006.01) |
| *B63C 11/26* | (2006.01) |
| *G08B 21/08* | (2006.01) |
| *A61B 5/08* | (2006.01) |

(52) U.S. Cl.
  CPC . *B63C 2009/0029* (2013.01); *B63C 2011/021* (2013.01); *B63C 2011/085* (2013.01)

(56) References Cited

U.S. PATENT DOCUMENTS

| | | |
|---|---|---|
| 7,988,511 B2 | 8/2011 | Bissell et al. |
| 2006/0012483 A1 | 1/2006 | Ethington |
| 2009/0036009 A1 | 2/2009 | Carl |
| 2009/0251321 A1 | 10/2009 | Delorey |
| 2009/0295566 A1 | 12/2009 | Weintraub |
| 2010/0182151 A1 | 7/2010 | Yang |
| 2010/0248567 A1 | 9/2010 | Carl |
| 2011/0294382 A1 | 12/2011 | Puls et al. |
| 2012/0269399 A1 | 10/2012 | Anderson et al. |
| 2013/0281795 A1 | 10/2013 | Varadan |

CONTROLLABLE WATER FLOATATION GARMENT

FIELD OF THE INVENTION

The present invention relates to a water floatation garment, and in particular, to such a garment incorporating a device for identifying emergency situation causing the garment to float to surface.

BACKGROUND OF THE INVENTION

Drowning can occur in various aqueous environments such as a pool, lakes, sea and/or ocean. Drowning does not necessitate that the person does not know how to swim, other factors may come into play that lead to drowning, such as head trauma, orientation loss, disorientation, loss of consciousness.

Various forms of floatation devices such as life vests, floaties, swim rings, variously shaped inflatable floatation devices. Some swimsuits have incorporated floatation device in the form of Styrofoam. However such Styrofoam and inflatable floatation device greatly limit the maneuverability and the ability to swim freely while wearing and/or associated with the floatation device.

SUMMARY OF THE INVENTION

There is an unmet need for, and it would be highly useful to have, a floatation garment that is controllable allowing deployment of a floatation means only when necessary. Such a controllable floatation device allows a user to use the garment without hindering swimming experience. The swimming garment of the present invention preferably provides a safety measure against accidental drowning within an aqueous environment such as a pool, lake, ocean or the like body of water.

The present invention is for a floatation swim garment that may be worn by a user and is preferably provided to sense a drowning events or the likelihood of such an event within a body of water. The swim garment preferably comprising at least one or more inflatable balloons and/or bladders that may be filled to cause a user to float and re-surface. Most preferably inflating the inflatable balloon is a controlled process that is controlled by way of a processor. Most preferably the inflating process is an event that is triggered by at least one or more sensed events where at least one or more threshold crossing event and/or rule based events occurs.

An optional embodiment of the present invention provides a water floatation garment incorporating sensors and electronic circuitry that identify a drowning incident to inflate at least one fillable bladder and/or balloon to form a floatation balloon that is integral with the garment. Most preferably the electronic circuitry may be deployed to inflate the floatation device only as is necessary for example when potential drowning incident is sensed.

Optionally the controllable floatation garment may be realized in optional forms for swimwear for example including but not limited to a dry suite, wet suite, swim shirt, diving vest, swim vest, diving buoyancy vest or the like.

Optionally the controllable floatation garment may be realized in the form of an add on garment, for example similar to a life vest however providing a user with full range of motion and/or flexibility for swimming.

Optionally the controllable floating garment may include at least two inflatable balloons. Optionally the controllable floating garment may include at least three inflatable balloons.

Optionally the inflatable balloons may be distributed on the garment so as to cause floatation of a user wearing the garment. Preferably the at least one inflatable balloon is distributed on the garment so as to ensure that the user's face is maintained out of the water once the user surfaces. Optionally an inflatable balloon may be disposed about the back of the neck and/or nape of a user.

Preferably the balloons and/or bladders may be inflated with an inflating module optionally provided in the form of a pyrotechnic reaction, prefilled gas container containing gas under pressure, an exothermic reaction releasing a flowing fluid in the form of gas, or the like process and/or reaction releasing a gas under pressure.

Optionally an individual inflatable balloon and/or bladders may be associated with an individual inflating module.

Optionally an inflating module may be associated with at least two or more inflatable balloons and/or bladders.

Optionally the garment may comprise a plurality of inflating modules according to and/or correlated to the number of inflatable balloons.

Optionally the inflatable balloons may be distributed along the garment corresponding with the user's right shoulder, left shoulder, and nape.

Optionally a further inflatable balloon and/or bladder may be provided and/or situated near and/or about the user's diaphragm.

Optionally the inflatable balloons may be distributed circumferentially, for example so as to surround the upper torso of a user. For example the inflatable balloons may be distributed so as to surround a user circumferentially for in at least one or more locations for example including but not limited to: surrounding the chest at or below the armpits, surrounding the shoulders, surrounding the waist area, the like or any combination thereof.

Optionally at least one inflatable balloon may be provided in the form of a fillable bladder and/or cuff that may be disposed and/or aligned with the user's diaphragm.

Optionally the inflatable balloon may be provided in the form of a low profile folded bladder. Optionally the inflatable balloon may be provided in the form of an encapsulated folded bladder.

Optionally the inflatable balloon and/or bladder may be provided form any material for example including but not limited to at least one more selected from latex, silicon, polymer, alloy, metal, metal alloy, polymer metal alloy, polymer alloy, synthetics, cloth the like or any combination thereof. Optionally the material may be provided from wearable material.

More preferably the inflatable balloon and/or bladder may be provided from materials characterized in that the material is configured to provide for holding air under pressure for a given period of time. More preferably the inflatable balloon and/or bladder may be provided from materials that are provide for holding air under pressure for up to about 15 minutes, and therein allow a user to float for at least 15 minutes. Most preferably the garment comprises a sensor module comprising a plurality of sensors most preferably integrated with and distributed about the garment. Optionally and preferably the sensor module comprises sensors for example including but not limited to movement sensor, accelerometer, three axis MEMS accelerometer, gyro sensor, depth sensor, pressure sensor, silicon piezoresistive pressure sensor, breath sensor, water sensor, pulse-oximeter, the like, or any combination thereof.

Optionally breath sensor may be realized as s respiration sensor in the form of a piezoelectric device that measures changes in thoracic and/or abdominal circumference during respiration, which may be utilized to indicate inhalation, expiration and breathing strength and can be used to derive breathing rate.

Optionally breath sensor may be realized in the form of a strain based sensor to measure the changes in the rib cage diameter by applying an elastic belt pressure to a strain gauge and measuring the resistance changes due to rib cage movements.

Optionally breath sensor may be provided in the form of a belt comprising at least one or more sensor for example including but not limited to a strain gauge and/or a piezoelectric sensor, induction belt sensor, Impedance pneumography sensor, the like or any combination thereof.

Most preferably the sensor module and inflation module may be controlled and/or functionally associated with electronic circuitry comprising a controller and communication module.

Optionally the electronic circuitry disposed in the controllable floatation garment may be controlled and/or in communication with an external controller and/or processing device. Optionally the external processor and/or controller may be provided in optional forms for example including but not limited to smartphone, computer, dedicated device, PDA, mobile communication device, hand held processing device, mobile processing device, or the like.

Preferably the external controller may be in wireless communication with the electronic circuitry and the controller and communication module integrated with the garment. Most preferably communication module may be provided in the form of Bluetooth low energy, Wi-Fi, or the like as is known in the art.

Optionally the device may further comprise a user interface that is functionally associated with the electronic circuitry and controller module. Preferably the user interface provides at least one of visible, audible and/or tactile cues and/or messages to a user prior to deploying and/or inflating at least one or more inflation balloon and/or bladder. Optionally the display may comprise at least one or more of a LED (light emitting diode), speaker, and/or tactile pad for example in the form of a piezoelectric pad, the like or any combination thereof.

Optionally user interface further comprises an override button and/or shutoff button and/or circuit breaker button provided to prevent deployment of at least one or more inflation balloon. Most preferably user interface override button provides a user with a small window of time within which balloon deployment may be circumvented by activation of an override button.

Optionally the garment according to optional embodiment of the present invention may be integrated with the sensors wherein optionally the garment thread may itself encase and/or envelope a sensor. Optionally the garment according the present invention may be provided from electronic textile providing for integrated sensors within the garment.

For example, electronic textiles (e-textiles) are fabrics that have electronics and interconnections woven into them, with physical flexibility and size that cannot be achieved with existing electronic manufacturing techniques. Components and interconnections are intrinsic to the fabric and thus are less visible and not susceptible to becoming tangled together or snagged by the surroundings. An e-textile may be worn in everyday situations where currently available wearable computers would hinder the user. E-textiles can also more easily adapt to changes in the computational and sensing requirements of an application, a useful feature for power management and context aware.

For example, electronic textile may be provided from piezoresistive fabric. Optionally piezoresistive fibers sensors can be produced when the used conductive yarn is coupled with an elastomer, for example Lycra to produce a multi-layered formation.

Optionally the inflatable balloons and/or bladder may be filled with at least one or more gaseous flowing fluid selected from air, carbon dioxide, nitrogen gas, inert gas, or the like.

Optionally the balloons and/or bladders may be filled by way of a chemical reaction releasing an expandable flowing fluid and/or a gas.

Optionally the balloons and/or bladders may be filled triggering a reaction signaling to inflate the balloons and/or bladder. Most preferably inflation is triggered with a trigger for example including but not limited to an electromagnetic trigger, mechanical trigger, chemical trigger, the like or any combination thereof. Optionally the trigger initiating the inflation may be provided in the form of a solenoid, spark plug, latch, a compressed bellow, the like or any combination thereof.

Optionally the inflatable balloon and/or bladder may be provided in various shapes and size, for example including but not limited to flat, cylindrical, spherical or the like.

Optionally the inflatable balloon and/or bladder may be distributed along the surface of the garment in any given pattern or formation. For example, the surface of the garment may have a plurality of inflatable balloons and/or bladders that form a matrix like configuration. Optionally the garment's surface may be distributed and/or dispersed with a plurality of fillable bladders in a matrix like pattern, checkerboard pattern, or any pattern.

Optionally the inflatable balloon may be provided form a single piece. Optionally the inflatable balloon and/or bladder may be provided from a plurality of balloons and/or bladders. Optionally the inflatable balloon and/or bladder may be provided from a plurality of interconnected balloons and/or bladders.

Optionally the plurality of balloons and/or bladders may be standalone having individual triggering events wherein each balloon and/or bladder is individually inflated. Optionally the plurality of balloons and/or bladders may be sequentially inflated and/or filled with at least one or more triggering event. Optionally the plurality of balloons and/or bladders may be collectively and/or substantially simultaneously inflated and/or filled with a single triggering element.

Optionally the inflatable bladder and/or balloon may be filled with at least one or more triggering events. Optionally the inflatable bladder and/or balloon may be filled with a plurality of controllable triggering events.

Optionally a plurality of controllable triggering events may be controlled at least with respect to triggering parameters such as timing, rate of inflation, the like or any combination thereof. For example, timing control may be configured such that the timing of a plurality of triggering events may be determined according to a pattern, for example including but not limited to sequential, simultaneous, gradual, intermittent, overlapping, contiguous, continuous the like or any combination thereof.

Optionally the inflatable balloon and/or bladder may be provided from a plurality of interconnected balloons and/or bladders having interconnecting passageways and/or interconnecting channels therebetween to facilitate filling and/or inflating.

The triggering mechanism most preferably brings about the inflation and/or filling of at least one or more balloons and/or bladders. Optionally the triggering signal may be provided so as to inflate at least one or more balloon and/or bladder by optional means for example including but not limited to a chemical reaction, electromagnetic spark, mechanical mixing of at least two or more agents, the like or any combination thereof. Optionally the triggering event may cause the reaction of Sodium Azide (NaN3) exothermic reaction to release and/or form nitrogen (N2) gas to inflate the floating bladders. Optionally the triggering event may cause the production carbon dioxide gas (CO2) by way of reacting Sodium Bicarbonate. Optionally the triggering event may trigger and/or cause the production a controlled polymerization reaction, for example provided to create foam (Styrofoam) within an inflatable bladder and/or balloon.

Optionally the triggering event may trigger and/or cause the release of a first reagent from a storage container allowing it to react with a second reagent that may be stored within the inflatable bladder, to cause the bladder to inflate. For example, the triggering event may activate a trigger, optionally in the form of a compressed bellow and/or electromagnetic trigger, causing the release of a first reagent, from a container, into an inflatable bladder comprising a second reagent, wherein the reaction between the first reagent and second reagent, produces a reaction inflating the bladder with a gaseous flowing fluid, for example carbon dioxide (CO2) or nitrogen gas (N2), and/or produces a controlled polymerization reaction provided to create foam, for example Styrofoam, within the volume of the inflatable bladder and/or balloon. Optionally two or more reagents may be stored and reacted within the inflatable bladder. Optionally two or more reagents may be stored and/or reacted within a single inflatable bladder. Optionally two or more reagents may be stored and/or reacted within at least two or more inflatable bladders.

Optionally inflation of at least one or more bladders may be provides for by a controllable mixing reaction between two or more reagents that are mixed to create a chemical reaction to inflate at least one or more bladder. Optionally a first reagent may be stored in a first bladder and a second reagent may be stored in a second bladder, wherein the first bladder and second bladder are isolated from one another with a seal, for example in the form of a controllable membrane and/or valve that are sensitive to a triggering event and/or signal, wherein the triggering signal provides for breaking the seal allowing the reagents to react with one another causing the first bladder and/or second bladder to inflate.

Optionally a single fillable bladder may comprise at least two or more reagents that are separated with a seal configured to be sensitive to a triggering event and/or signal. Preferably a triggering event and/or signal provides for breaking the seal internal within a fillable bladder allowing the at least two or more reagents to react within the bladder, causing the bladder to inflate. Optionally the seal internal with the inflatable bladder may be provided in the form of a valve and/or membrane.

Embodiment of the present invention may utilize a proprietary scoring method to determine the emergency state for each sensor with respect to threshold value that is cumulatively scored to determine the drowning probability. Optionally the sensor data gathered and utilized to determine the emergency situation may for example includes data selected from: garment depth, limb movements, respiration, time stamp, under water flag, the like or combination thereof.

Within the context of this application the terms balloon and bladder may be used interchangeably in referring to a container or volume capable expanding in going from a small volume to a larger volume. The bladder may be filled with different materials for example including a gaseous flowing fluid, a flowing fluid, polymerizing agents, foamable material, foam, or the like.

Within the context of this application the term filling and/or inflating may be used interchangeably to refer to the act of filling the bladder with an expanding medium for example a flowing fluid, a gas, a gaseous flowing fluid, foam, the like or any combination thereof, so as to cause the garment to float.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

Unless otherwise defined the various embodiment of the present invention may be provided to an end user in a plurality of formats, platforms, and may be outputted to at least one of a computer readable memory, a computer display device, a printout, a computer on a network or a user.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

It should be noted that optionally any device featuring a data processor and/or the ability to execute one or more instructions may be described as a computer, including but not limited to a PC (personal computer), a server, a minicomputer, a cellular telephone, a smart phone, a PDA (personal data assistant), a pager, or the like. Any two or more of such devices in communication with each other, and/or any computer in communication with any other computer may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A shows an optional embodiment in the form of a swimming garment, FIG. 1B shows an optional embodiment in the form of a diving garment;

DESCRIPTION OF THE PREFERRED EMBODIMENTS

The principles and operation of the present invention may be better understood with reference to the drawings and the accompanying description. The present invention is for a swim garment that may be worn by a user and is preferably provided to sense a drowning events or the likelihood of such an event within an aqueous environment. The swim garment preferably comprising at least one or more fillable bladders that may be inflated and/or filled with materials to cause a user to float and re-surface, most preferably resurfacing face up.

Preferably inflating and/or deploying the fillable bladder (inflatable balloon) may be a controlled process that is controlled by way of a processor. Most preferably the inflating process is a triggered event that is triggered based on at least one or more sensed events. Such sensed events may for example comprise threshold crossing, wherein at least one or more threshold crossing events and/or rule based events occur to initiate and/or trigger inflation and/or filling of the inflatable bladder.

The following figure reference labels are used throughout the description to refer to similarly functioning components are used throughout the specification hereinbelow.

Figure 1:
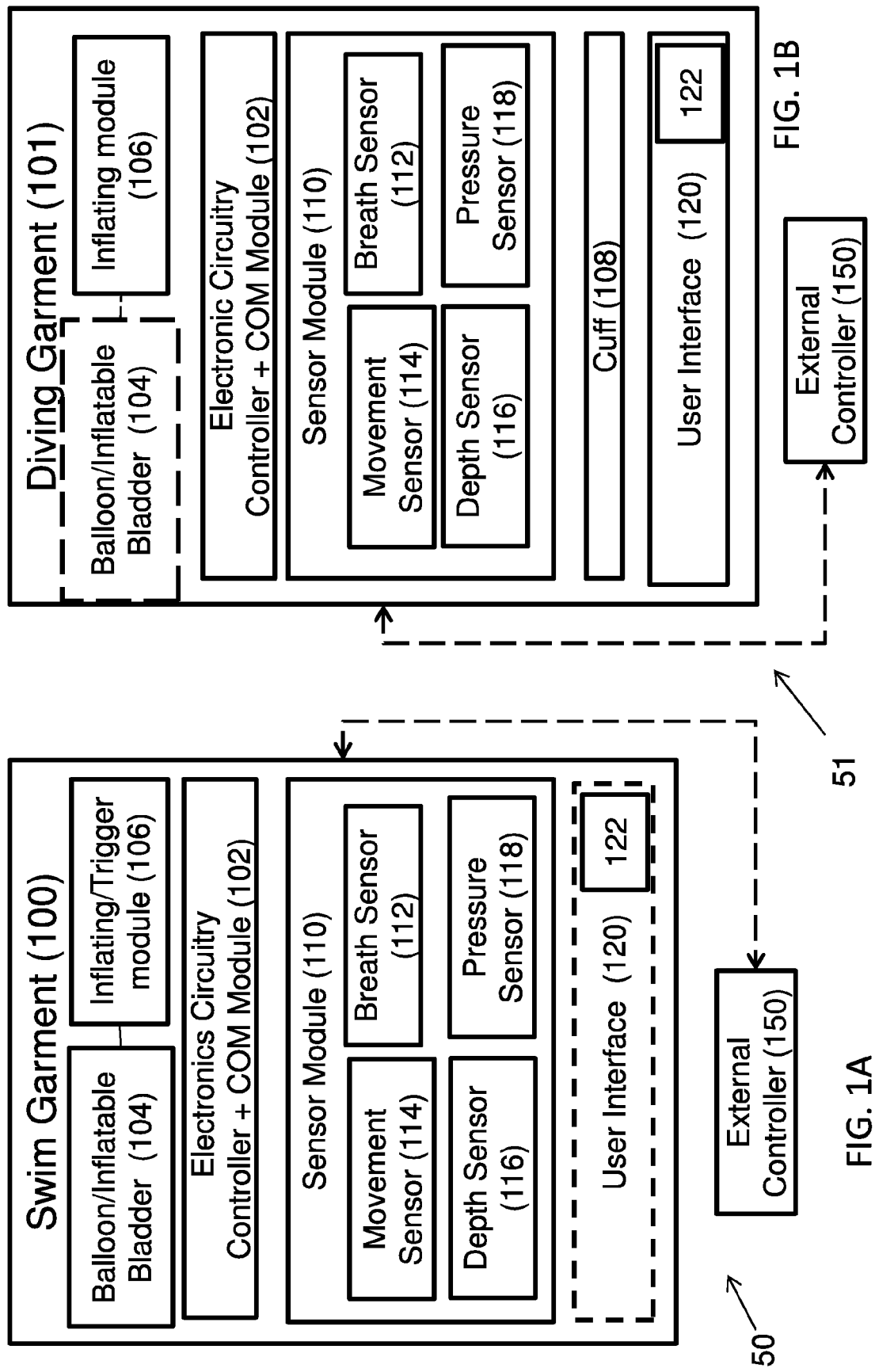
FIG. 1A-B are schematic block diagrams of optional device and system according to an optional embodiments of the present invention.

50 swim system;
51 diving system;
100 swim garment;
101 diving garment;
102 controller and communication module;
104 inflatable balloon/bladder;
106 inflating module;
108 inflatable cuff;
110 sensor module;
112 breathing sensor;
114 movement sensor;
116 depth sensor;
118 pressure sensor;
120 user interface;
122 override;
150 external controller;

Referring now to the drawings, FIG. 1A is a schematic block diagram of an optional swim garment 100 and system 50 according to an optional embodiment of the present invention. Floatation swim garment 100 comprises electronics and sensors that are incorporated and/or integrated within the swimming garment.

Optionally the swimming garment 100 may be provided in optional form for example in the form of a bathing suit, swim shirt, wet suite, dry suit or the like.

Optionally garment 100 may be provided as add-on garment that may be placed over an off the shelf swim garment converting it to a safety floatation device while providing full range of motion for the off the shelf swim garment.

Floatation swim garment 100 comprises a controller and communication module 102, a sensor module 110 and at least one or more inflatable balloons 104 corresponding with a triggering and/or an inflating module 106. Optionally swim garment 100 may further comprise an optional user interface 120 for example provided in the form a display, LED display, LED indicator, or the like.

Floatation swim garment 100 comprises at least one inflatable balloon and/or bladder 104 that may be inflated with an inflation module 106 based on a triggering control signal received from a controller module 102.

Optionally user interface 120 may further comprise an override button 122 may interrupt the control signal and negate the control signal via controller module 102, therein overriding and/or interrupting the functions of inflating module 106.

Most preferably the control signal generated by controller module 102 may be rendered based on analysis of at least one or more sensed events to determine likelihood of drowning event or the like life threatening event. Preferably the sensed events may be provided and/or determined with at least one or more sensors comprising sensor module 110.

Optionally inflating triggering signal generated with controller module 102 based on a threshold crossing event, or a rule based event identified by controller module 102. Optionally the threshold event limitation and/or rule based event may be communicated to controller module 102 via an optional external controller device 150. Optionally and preferably external controller device 150 may be in wireless communication with controller module 102 to identify the rules and thresholds associated with user using swim garment 100.

System 50 preferably includes garment 100 and external controller device 150. Preferably external controller device 150 may be utilized to communicate threshold such as depth limitation, time limitations or the like. Optionally device 150 may be realized as a parent control unit via a smartphone optionally via a dedicated app to set such limitation.

Optionally system 50 may be utilized to communicate to emergency services or the like initial response services when a drowning event is identified.

Optionally triggering events and/or rules for initiating emergency protocol and inflation of balloon may for example include but is not limited to at least one or more of: depth threshold, time based threshold, activity threshold, any combination thereof or the like. Optionally triggering events may be based on identified sensed events provided by at least one or more sensors disposed in sensor module 110 provided with garment 100. Optionally the trigger event and threshold rules may be predefined by the device and stored with controller module 102.

Optionally the trigger event and threshold rules, provided to inflate device 100 may be defined by a user and/or government body and/or agency or the like and communicated to controller module 102 through external controller 150.

Optionally controllable floatation garment 100 may be realized in optional forms for swimwear for example including but not limited to a dry suite, wet suite, swim shirt, diving vest, swim vest, or the like.

Optionally controllable floating garment 100 may include at least two inflatable balloon and/or bladders 104. Optionally floating garment 100 may include at least three inflatable balloon. Optionally swim garment 100 may comprise a plurality of interconnected inflatable bladders and/or balloons 104.

Optionally inflatable balloons 104 may be distributed in any manner on the garment 100 so as to cause the user wearing the garment 100 to float once the triggering event has been sensed, while permitting for enjoyable swimming experience.

Preferably at least one inflatable balloon 104 is disposed on the garment so as to ensure that the user's face is maintained out of the water once the user surfaces. Optionally at least one inflatable balloon 104 may be disposed about the back of the neck and/or nape of a user.

Preferably balloons 104 may be inflated with an inflating and/or triggering module 106 that may be provided in optional forms. Optionally inflating module 106 may for example be provided in at least one or more form including but not limited to a controlled pyrotechnic reaction, a polymerization reaction, a chemical reaction, an electromagnetic event, a prefilled gas container containing gas (for example $CO_2$, compressed air, nitrogen gas ($N_2$)) under pressure, an exothermic reaction releasing a flowing fluid in the form of gas, exothermic reaction, or the like process. Optionally the inflating/triggering module 106 provides a controllable reaction releasing an expandable gas under pressure. Optionally the inflating/triggering module 106 provides and/or facilitates performing a controlled chemical reaction to cause bladders 104 to expand and/or inflate due to at least one or more methods selected from a chemical reaction, a polymerization reaction, a mixing reaction, electromagnetically triggered reaction, that leads to the substantially instantaneous inflation of bladder and/or balloon 104.

Optionally an individual inflatable balloon 104 may be associated with an individual inflating module 106.

Optionally an inflating module 106 may be associated with at least two or more inflatable balloons 104 that may be interconnected with one another.

Optionally garment 100 may comprise a plurality of inflating module 106 according to and/or correlated to the number of inflatable balloons 104 utilized.

Optionally inflatable balloons 104 may be dispersed and/or distributed along the garment in any pattern or form corresponding with the user. Preferably the distribution pattern of balloon 104 along the surface of garment 100 is configured to optimize floatation of the user.

Figure 2:
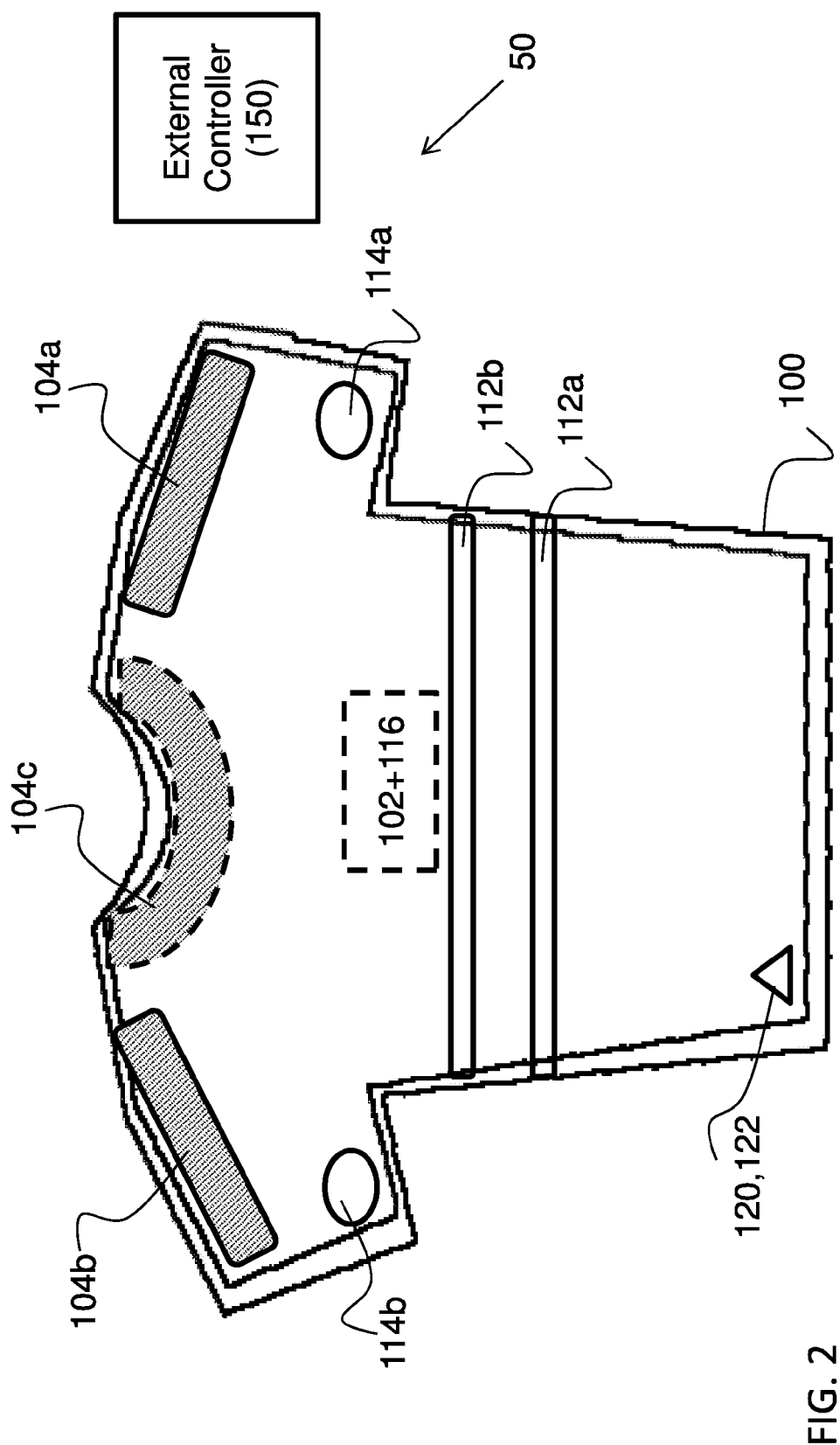
FIG. 2 is a schematic illustration of a swimming garment according to an optional embodiment of the present invention.

Optionally at least one or more balloon 104 may be aligned with at least one of a user's right shoulder, left shoulder, and nape (back of the neck), for example as shown in FIG. 2.

Optionally at least one or more bladders 104 may be distributed along garment 100, for example as shown in FIG. 3A-D.

Most preferably garment 100 includes a sensor module 110 that comprises at least one or more sensors most preferably integrated with and dispersed about the garment. Optionally and preferably the sensors may be distributed along garment 100 based on their intended function. Optionally and preferably sensor module 110 comprises sensors for example including but not limited to movement sensor 114, sensor 116, pressure sensor 118, breath sensor 112, pulse-oximeter, water sensor, the like, or any combination thereof.

Optionally movement sensor 114 may for example be realized in optional forms for example including but not limited to accelerometer, gyro sensor, a three axis accelerometer, the like or any combination thereof, and provided for identifying the movement and/or orientation of the user wearing garment 100.

While sensor 114 may be disposed at any portion of garment 100, optionally, movement sensor 114 may be disposed about the sleeves of garment 100 so as to detect movement of extremities. For example when disposed about the sleeves a movement sensor 114 optionally provided in the form of an accelerometer could indicate flapping motion characteristic of a struggling individual that may be indicative of drowning. Optionally movement sensor 114 provides for identifying drowning according to the movement. Optionally movement sensor 114 may for example be realized in the form of accelerometer, gyro sensor, the like or any combination thereof.

Breathing sensor 112 may be provided in optional forms to detect directly or indirectly if the user is breathing. Optionally breathing sensor 112 may be provided in optional forms for example including but not limited to: a pulse-oximeter, a piezoelectric pad, a piezoelectric belt and/or band, an electromagnetic induction sensor. For example a piezoelectric belt may be fit within garment 100 so as to surround the user's upper torso and ribcage so that chest movement associated with breathing may be monitored. Preferably breath sensor 112 may be utilized to sense the continuous breathing state of a user, or detect a breathing pattern that may for example be associated with drowning.

Optionally breathing sensor 112 may be realized in the form of a piezoresistive electronic textile that is wholly integrated within the garment itself.

Most preferably sensor module 110 and inflation module 106 may be controlled and/or functionally associated with electronic circuity including a controller and communication module 102.

An optional device user interface 120 may be functionally associated with controller module 102. Preferably user interface 120 may provide at least one of visible and/or audible and/or tactile cues and/or messages to a user prior to triggering and/or deploying and/or inflating at least one or more inflation balloon and/or bladders 104. Optionally the display 120 may comprise at least one or more of a display, LED indicator, LED, speaker, and/or tactile pad for example in the form of a piezoelectric pad capable of vibrating, the like or any combination thereof.

Optionally user interface 120 may further comprise an override button 122 and/or shutoff button and/or circuit breaker button provided to prevent deployment of at least one or more inflation balloon and/or bladder 104. Most preferably user interface override button 122 provides a user with a small window of time within which balloon deployment may be circumvented by activation of an override button 122.

Optionally controller and communication module 102 disposed in garment 100 may be controlled and/or in communication with external controller 150 and/or processing device. Optionally the external processor and/or controller 150 may be provided in optional forms for example including but not limited to smartphone, computer, dedicated device, PDA, mobile communication device, hand held processing device, mobile processing device, or the like.

Preferably system 50 is formed by the combination of swimming garment 100 in communication with external controller device 150. Preferably external controller device 150 may be utilized to communicate threshold such as depth limitation, time limitations or the like. Optionally device 150 may be realized as a parent control unit via a smartphone optionally via a dedicated app to set such limitation.

Preferably external controller 150 may be in wireless communication with the controller and communication module 102 integrated with the garment 100. Most preferably communication module may be provided in the form of Bluetooth, Bluetooth low energy, Wi-Fi, or the like as is known in the art.

Optionally controller 150 may be utilized to set an alarm state when necessary and so as to communicate the alarm state to a third party for example including but not limited to next of kin, emergency services, and/or rescue service or the like.

FIG. 1B shows an optional embodiment of the present invention for a controllable floatation garment 101 realized in the form of a diving suite and/or diving vest and/or diving buoyancy vest. Garment 101 is similar to garment 100, having similar sensors and components as previously described, and in that it may be utilize to form a system 51 including garment and external processing unit 150. As previously described external processing unit 150 may be utilized to set limitation for determining when to activate inflation module 106. For example processing unit 150 may be provided to set a depth limit and/or threshold and/or a time limit and/or threshold for diving garment 101.

Garment 101 is specialized in the form of a diving vest and/or suite and/or most preferably diving buoyancy vest may utilizing a diving buoyancy vest's internal buoyancy bladders and further comprising preferably with an additional specialized inflatable balloon and/or bladder 108, provided to prevent lung tearing and/or lung collapse for example experienced when a diver surfaces too fast and/or during emergency surfacing due to a situation sensed with sensors module 110.

Optionally the specialized inflatable balloon 108 may be provided and/or situated near and/or about the user's diaphragm. Optionally at least one inflatable balloon 108 may be provided in the form of a fillable bladder and/or cuff that may be disposed and/or aligned with the user's diaphragm so as to prevent tearing of the lung during an emergency surfacing leading to a quick ascension to the surface, that could otherwise lead to a torn lung due to trapped air. Accordingly inflatable balloon 108 could circumvent such a torn lung event by mechanically forcing air out of the lungs while the diver ascends to the surface. Most preferably cuff 108 is inflatable with inflating module 106, as previously described with fillable bladder and/or balloon 104.

Optionally garment 101 may be provided with additional optional inflatable balloons 104, most preferably when garment 101 is not provided in the form of a diving buoyancy vest having intrinsic buoyancy balloons.

Optionally garment 101 may further be specialized in that controller module 102 and inflating module 106 may interact continuously to provide accurate and consistent depth control. Optionally and preferably controller module 102 and inflating module 106 may further provide for depth and ascension control of a diver utilizing garment 101 so as to prevent the need for decompression once the diver surfaces while maintaining diver safety.

Now referring to FIG. 2 and FIG. 3A-D showing optional configurations of swimming garment 100 depicted in FIG. 1A. FIG. 2 provides a schematic illustrative depiction of an optional swimming garment 100 within system 50, shown in the form of a swim shirt, having a plurality of inflatable balloons 104. Garment 100 may be configured to comprise at least three inflatable balloons 104*a,b,c*, wherein balloons 104*a,b* are disposed about each shoulder, while balloon 104*c* is dispose to correspond to the user's back of the neck and/or nape so as to ensure that the user surfaces having the face out of the water.

Most preferably garment 100 comprises a sensor module 110 dispersed about its surface to indicate and provide an indication of the probability of drowning. For example as shown, sensor module 110 may comprise at least two motion sensors 114*a, b* that are disposed along the sleeve of garment 110 to identify drowning event. For example, arms flailing and/or rapidly moving in an up-down motion or in circumferential treading pattern, would be sensed by motion sensors 114*a,b* and conveyed to the controller module 102 to contribute to the decision of issuing a triggering signal so as to trigger inflation module 106 (not shown) to inflate balloons 104*a,b,c*. Optionally motion sensors 114*a,b* may be provided in the form of an accelerometer to detect arm movement.

Additional sensor integrated with garment 100 may preferably be at least one breathing sensor 112. Breathing sensor 112 may be realized as is shown in the form of two piezoelectric belts 112*a,b* upper and lower utilized to detect respiration and chest movement to determine a user's breathing pattern and/or state. Optionally breathing sensor 112 may be realized in the form of a pulse-oximeter, piezoelectric pad, or electromagnetic induction sensor. Optionally and preferably the data collected by breathing sensor 112,112*a*,112*b* may be collected by controller 102 to facilitate the decision to trigger inflation of at least one or more balloons 104 with trigger inflation module 106.

Most preferably garment 100 comprises depth sensor 116 utilized to determine if a depth limit has been breached by the user associated with garment 100.

Optionally and preferably garment 100 is further fit with a sensor capable of detection if the garment is under water or not to provide an underwater state and/or flag that may be communicated to controller 102 so as to determine if a true drowning situation exists. For example, if a water sensor indicates that garment 100 is not in water and/or under water then a triggering event will not take place as the likely the user is in dry environment not conducive to drowning.

Most preferably controller module 102 is provided to identify and determine the relative drowning risk associated to a user associated with garment 100. Optionally if a drowning situation is identified by module 102, preferably based on sensed data received from sensor module 110, module 102 may communicate this to user interface 120, comprising an optional override button 122. Most preferably unless override button 122 is pressed within a given timeframe, controller module 102 will proceed to inflate at least one or more bladders/balloon 104. Optionally UI 120 may be provided as a tactile, visual or audible cue to the user indicative of the sensed state. Optionally controller module 102 may further comprise a learning module that is provided to customize garment 100 according to its user preferably following a training period where sensor data is gathered.

As previously described an optional external controller 150 in wireless communication with controller module 102, wherein controller 150 may be utilized to communicate depth limitation, time limitation or the like parameters that may be utilized to determine the likelihood of a drowning incident.

Optionally controller module 102 may communicate to controller 150 whenever the likelihood of a drowning incident increases beyond a predefined threshold.

Figure 3B:
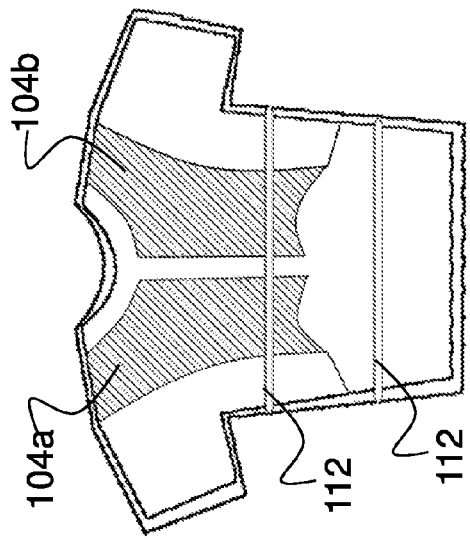
FIG. 3A-D are schematic illustrations of a swimming garment showing different configurations of the inflatable bladder according to optional embodiments of the present invention.
Figure 3C:
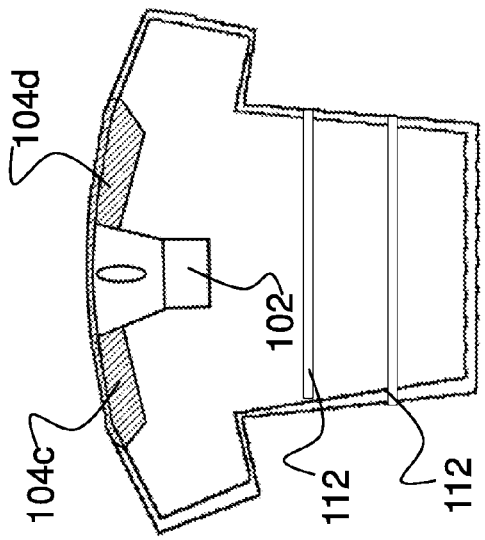
Figure 3A:
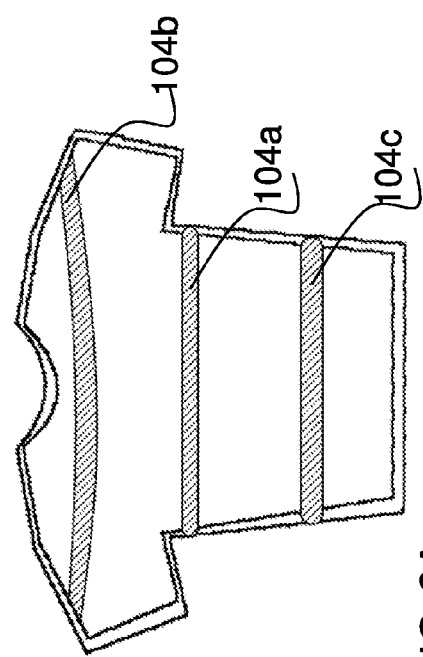

FIG. 3A shows an optional embodiment of garment 100 showing optional locations of a plurality of fillable bladders and/or balloon 104 along the surface of garment 100, provided in the form of circumferential fillable bladders 104. For visual clarity only the balloons 104 are shown. As shown, garment 100 may be fit with at least one or more fillable bladders 104a-c configured to surround the user's body along different anatomical locations surrounding the upper torso, for example including but not limited to under armpits 104a, along waist 104c, above shoulders 104. Optionally garment 100 may comprise at least one or more such circumferential fillable bladders 104a-c shown in FIG. 3A.

Figure 3D:
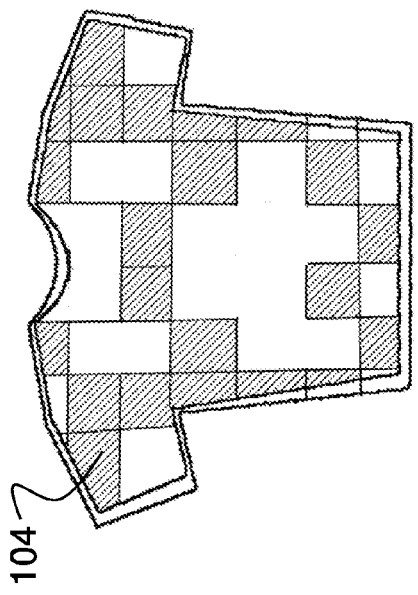

FIG. 3D shows a further optional embodiment of garment 100 wherein a plurality of interconnected bladders 104 are utilized to form a matrix like network of interconnected inflatable bladders 104 along garment 100. Optionally the pattern formed of interconnected bladders 104 may be configured according to the size of the user and/or garment 100, may be determined to assume a shape that is most conducive to achieving floatation. Optionally each of the bladders 104 distributed along garment 100 may be individually or collectively controlled with triggering module 106 and controller 102 to determine the timing and triggering pattern required.

FIG. 3B-C show an optional embodiment of garment 100 where FIG. 3B shows the front side and FIG. 3C shows the back side. FIG. 3A shown the front inflatable bladders 104a,b and breathing sensor 112 in the form of two piezoelectric belts 112 acting as a breathing sensor, other sensors as previously described such as movement sensor are not shown for the purpose of clarity.

FIG. 3C shows the back side of garment 100 where electronic circuitry and controller module 102 are schematically shown. The back side of garment 100 features a further fillable bladder 104c,d corresponding to the user's shoulders. Optionally and preferably bladders 104c,d may be provided in the form of an encapsulated folded bladder that is configured to expand with a controlled triggering signal provided by controller 102 and triggered with trigger module 106 (not shown) to cause the substantially instantaneous filling of bladders 104a-d so as to cause the user to float.

As previously described the triggering agent and inflating means may be selected according to at least one or more of chemical reaction producing an expandable gas, mixture of two or more reagents, polymerization reaction or the like.

Figure 4A:
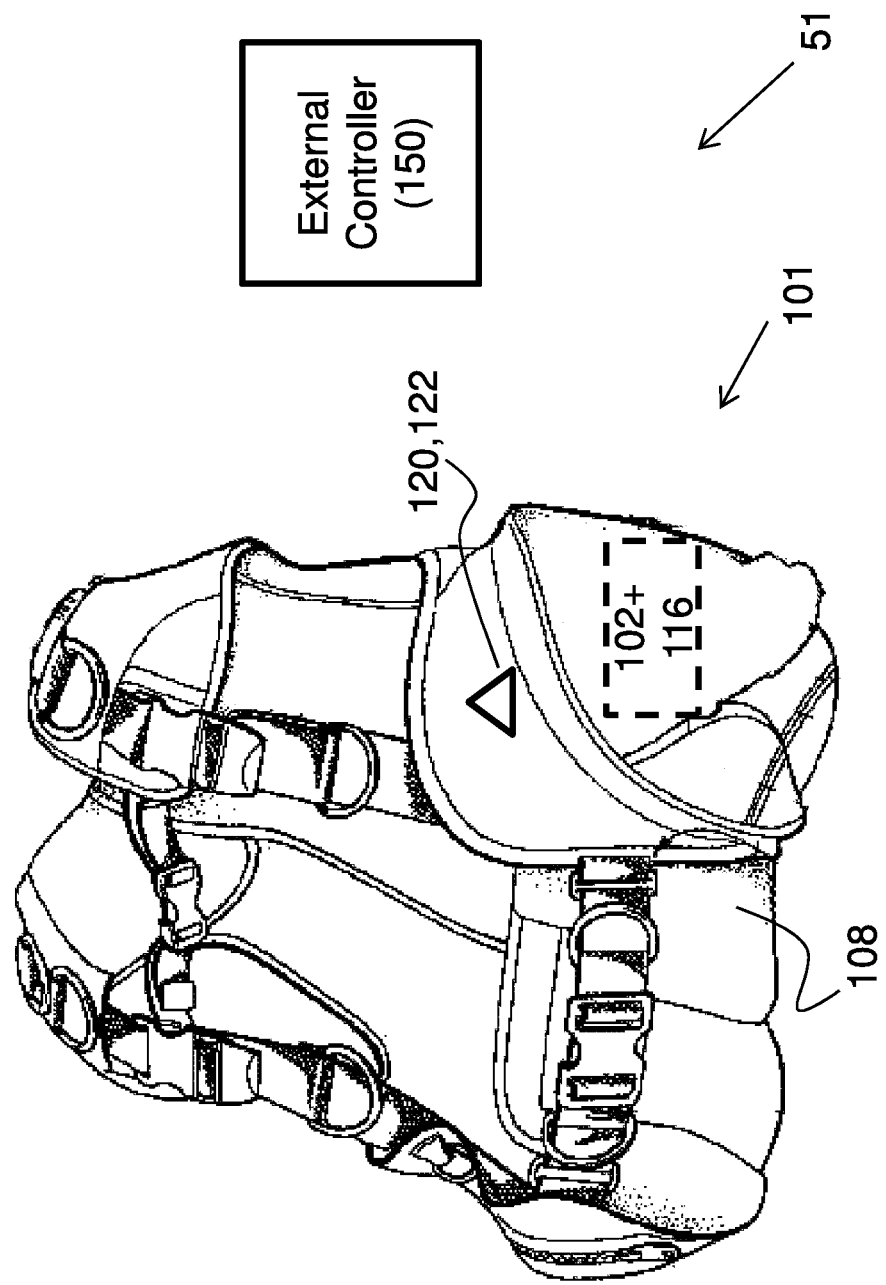
FIG. 4A-C are schematic illustrations of a diving garment and system according to optional embodiments of the present invention.
Figure 4B:
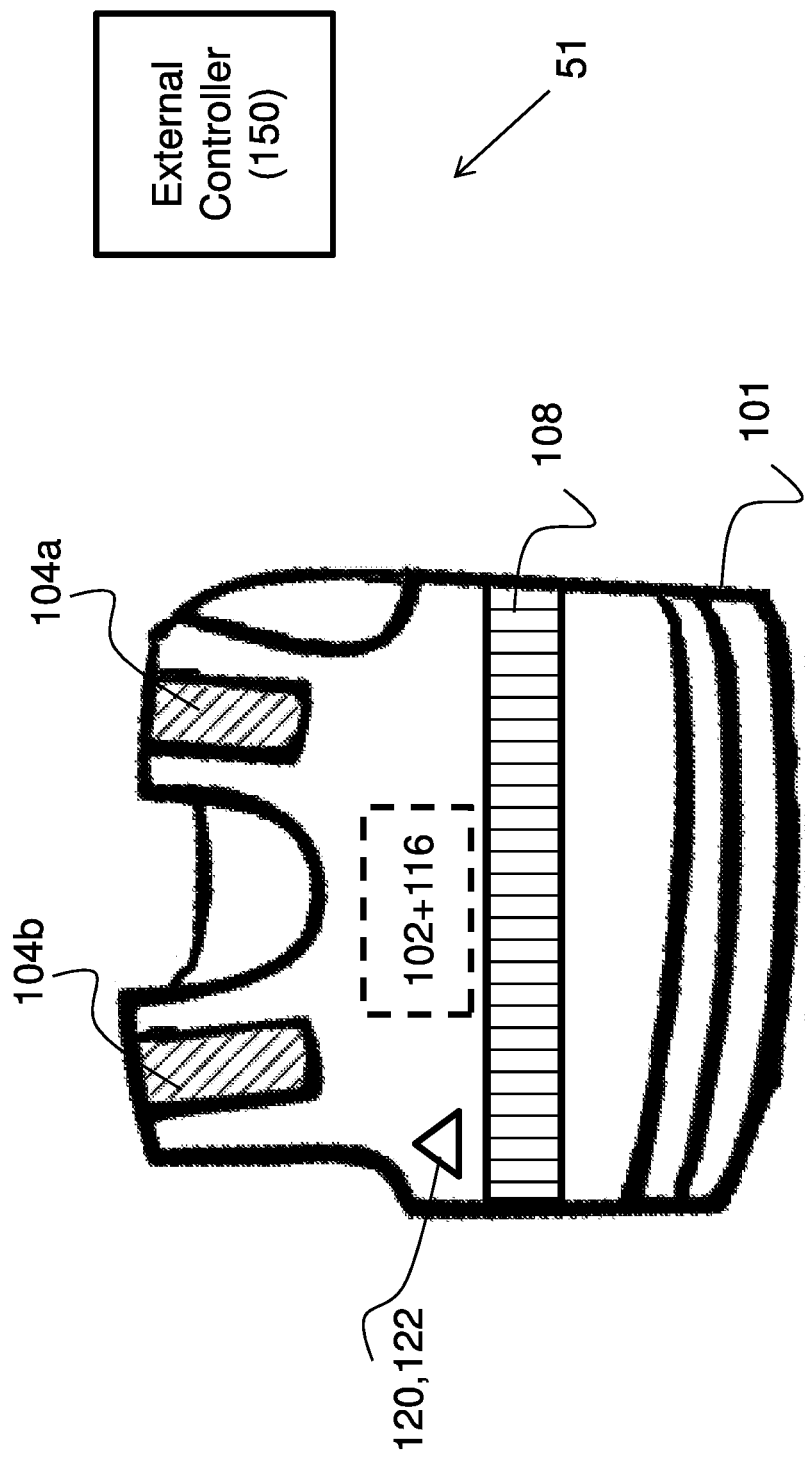
Figure 4C:
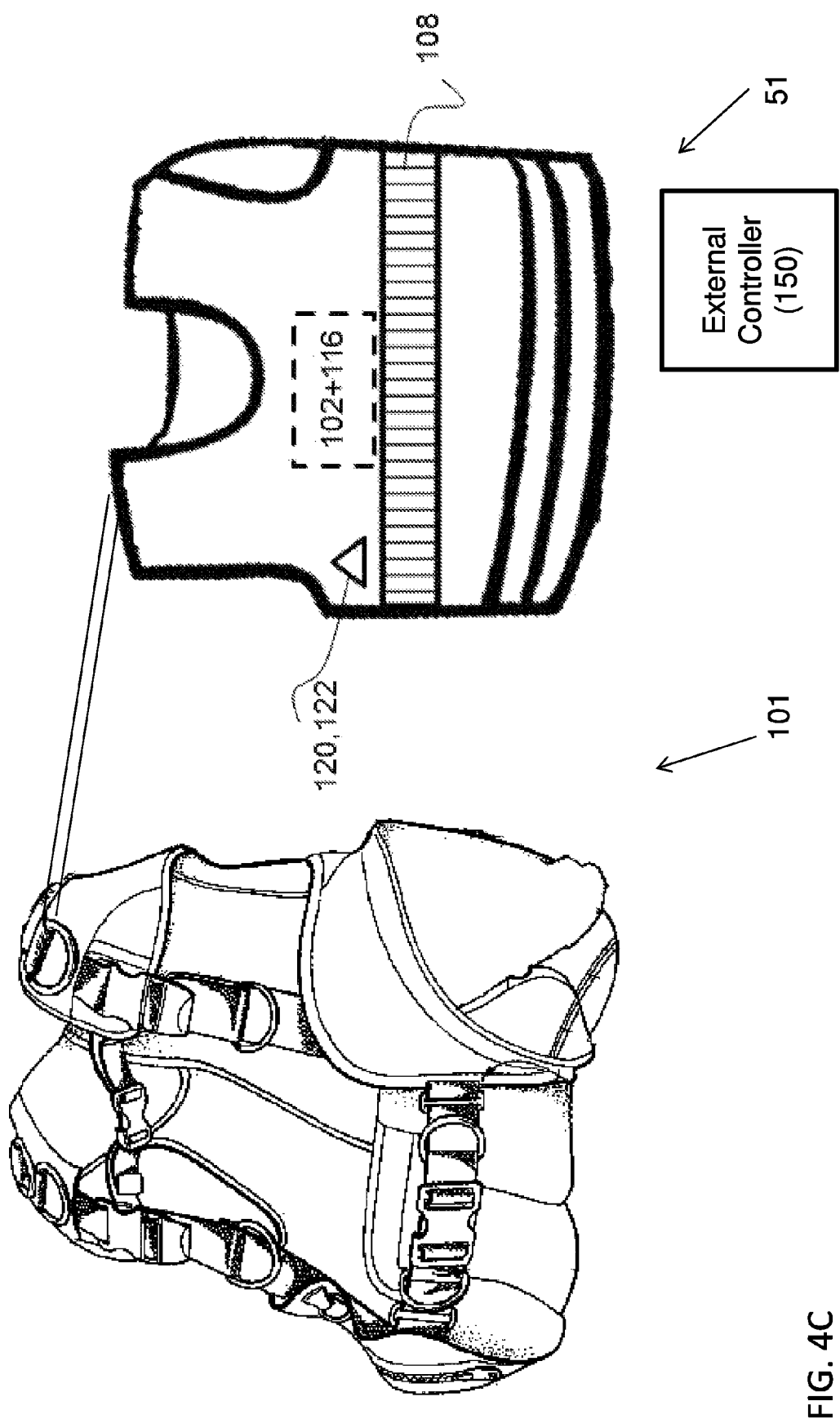

Now referring to FIG. 4A-C showing optional embodiments of a diving garment 101 as described in FIG. 1B.

FIG. 4A shows a diving garment 101 provided in the form of a buoyancy vest having intrinsic bladders and/or balloon that may inflate to control a diver's buoyancy via controller module 102 and depth sensor 116. The buoyancy vest including a cuff 108 placed within the buoyancy vest so as to align with a diver's diaphragm. Most preferably cuff 108 is inflated during emergency situations when emergency surfacing is required, so as to prevent the diver from suffering from a torn lung. Most preferably cuff 108 is inflated via inflation module 106 (now shown) that is functionally associated with controller module 102 and depth sensor 116

Optionally and preferably garment 101 in the form of a buoyancy vest may comprise a user interface 120 and override button 122 as previously described.

FIG. 4B shows a similar controllable inflation garment 101 in the form of a diving vest 101. The diving vest 101 characterized in its inclusion of a specialized inflatable balloon 108 that may be inflated to prevent tearing of the lung when surfacing quickly while diving.

Optionally diving vest 101 may not include breathing sensor 112 provided in swim shirt 100.

FIG. 4C shows a similar controllable inflatable garment 101 comprising inflatable balloon 108 and controller module 102 and depth sensor 106, provided in the form of a swim shirt 101 that may associated with and worn beneath a state of the art a buoyancy vest. Preferably controller module 102 may be coupled with vest and provide for inflating the buoyancy vest as is necessary according to analysis provided by module 102. Optionally module 102 may be provided to inflate the vest as well as balloon 108.

Figure 5:
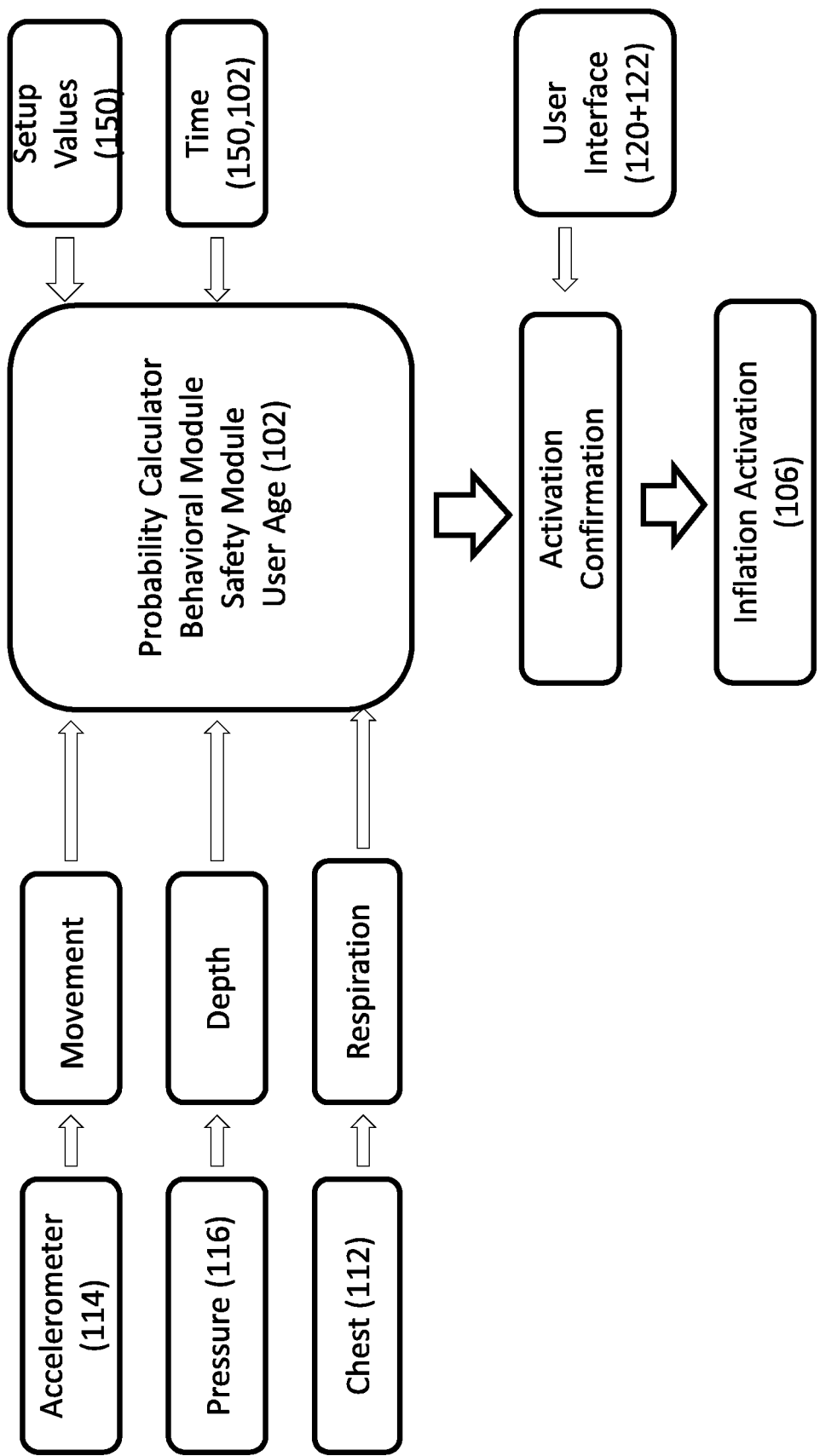
FIG. 5 is a block diagram chart showing the method of use of the device and system according to the present invention.

FIG. 5 shows a block diagram of the information flow in an optional swim garment 100 integrated with a plurality of sensor and a controller module to produce a control signal to inflate the garment so as to prevent an/or reduce the probability of a drowning incident, as previously described. Central to the method is processor module 102 that provides for determining the likelihood of a drowning incident based on a plurality of sensors disposed in sensor module 110, for example including but not limited to a breathing sensor 112, depth sensor 116, and movement sensor 114, pressure sensor 118, water sensor, that are functionally associated with controller 102.

Most preferably controller 102 comprises a probability calculator to determine the likelihood of a drowning incident based on a plurality of data for example including but not limited to a priori data, derived data. Optionally the data and/or parameters may for example include but is not limited to user's age, behavioral modeling, limitations set by a user, predefined limitations, safety standards, any combination thereof or the like.

Optionally some of the data and/or parameters may be communicated to controller 102 from an external processor 150 for example in the form of a parental limitation and/or setup values, for example the limit to the depth the garment is allowed to be in. Optionally once controller 102 has determined likelihood of a drowning incident that may be communicated to a user for confirmation via an optional interface module 120 so as to provide the opportunity to override the situation via an optional override button 122. Preferably if the control signal is not deactivated via button 122 the control signal is sent to inflation module 106 to inflate the garment's balloon (104, not shown).

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

What is claimed is:

1. A swimming garment for preventing a drowning incident, the swim garment having an integrated apparatus for identifying a potential drowning incident and for inflating at least one fillable bladder for surfacing a user, the apparatus comprising:
    a) electronic circuitry module having power module, processing module and communication module; said processing module provided to determine a user's drowning probability score and to initiate a response according to said drowning probability score by communicating a triggering signal to activate an inflating module that is functionally coupled with and utilized to inflate said at least one fillable bladder;
    b) said processing module functionally associated with a sensor module comprising a plurality of sensors including: at least one breathing sensor, at least two movement sensor, a depth sensor, a pressure sensor, and a water sensor; wherein said processing module provides for processing data provided from said sensor module to determine said drowning probability score; characterized in that:
        i) said at least two movement sensors are provided in the form of an accelerometer disposed about a portion of the garment corresponding to the arm's sleeves; and
        ii) said breathing sensor is provided in the form of a belt configured to measure changes in thoracic and/or abdominal circumference during respiration; and characterized in that said movement sensors are configured to detect drowning based on the movement of a user's arms.

2. The garment of claim 1 wherein said breathing sensor is provided in the form selected from:
    a) piezoelectric pad;
    b) electronic textile in the form of a piezoelectric element that is woven into the garment;
    c) a pulse-oximeter;
    d) a piezoelectric belt;
    e) a piezoelectric band;
    f) an electromagnetic induction sensor;
    g) a belt comprising a strain gauge;
    h) a belt comprising piezoelectric sensor,
    i) a belt comprising an induction belt sensor;
    j) a belt comprising an impedance pneumography sensor, and
    k) any combination thereof.

3. The garment of claim 1 wherein said fillable bladder is an encapsulated folded bladder.

4. The garment of claim 1 wherein said fillable bladder is provided from materials selected from the group consisting of: latex, silicon, cloth, polymer, polymer alloy, metallic alloy, metal, polymer metal alloy, synthetics, and any combination thereof.

5. The garment of claim 1 wherein said fillable bladder is provided from semipermeable material.

6. The garment of claim 1 wherein said inflating module further comprises at least one or more prefilled gas container containing gas selected from the group: air, carbon dioxide (CO2), nitrogen (N2) and any combination thereof.

7. The garment of claim 1 further comprising a user interface provided for communicating with the user prior to inflating said at least one bladder, wherein user interface communication is selected from the group consisting of at least one of: visible cues, audible cues, tactile cues, or any combination thereof.

8. The garment of claim 7 further comprising an override button.

9. The garment of claim 1 wherein said sensor module comprises at least two breathing sensors.

10. The garment of claim 1 wherein at least one inflatable bladder is provided to encircle the upper torso of the user form a position selected from the group consisting of: under the armpits, around the shoulders, along the waist, configured to be aligned with the user's diaphragm and any combination thereof.

11. The garment of claim 1 comprising a plurality of inflatable bladders distributed about the surface forming a matrix of interconnected inflatable bladders.

12. The garment of claim 11 wherein said plurality of inflatable bladders are controlled in a manner selected from:
    a) uniformly controlled with a single triggering signal;
    b) individually controlled with a plurality of individual triggering signals;
    c) controlled with at least one triggering signal; or
    d) controlled with a plurality of controllable triggering signals.

13. The garment of claim 12 wherein said plurality of inflatable bladders are controlled with a plurality of controllable triggering signals; controlled at least with respect to triggering parameters selected from: time, rate of bladder inflation, and any combination thereof.

14. The garment of claim 12 wherein said triggering signals may be controlled according to any pattern selected from the group consisting of: sequential, simultaneous, gradual, intermittent, overlapping, contiguous, continuous, and any combination thereof.

15. The garment of claim 1 wherein said inflating module provides for filling at least one or more bladders, with a triggering signal provided with said controller module by inflating means selected from the group consisting: a chemical reaction, an electromagnetic spark, mechanical mixing of at least two or more stored reagents, mechanically releasing gas from a confined storage container, polymerization reaction, a controlled pyrotechnic reaction, exothermic reaction releasing gas, controllably reacting Sodium Azide (NaN3) to form Nitrogen (N2) gas, controllably reacting Sodium Bicarbonate to produce carbon dioxide gas (CO2), controllable polymerization reaction for producing foam within at least one inflatable bladder, and any combination thereof.

16. The garment of claim 15 wherein said triggering module provides for a controllable mixing reaction where two or more reagents are mixed to create a chemical reaction to inflate the bladder, wherein a first reagent is stored in a first bladder and a second reagent is stored in a second bladder, wherein said first bladder and said second bladder are isolated from one another with a seal, and wherein a triggering signal provides for breaking said seal allowing the reagents to react with one another causing the inflation of at least one or both of said first bladder or said second bladder.

17. The garment of claim 1 wherein said triggering signal is an electromagnetic signal provided for controlling an electromagnetic element selected from the group consisting of a solenoid, motor, valve, a compressed bellow, any combination thereof.

18. The garment of claim 1 wherein an inflatable bladder comprises two or more reagents separated by an internal seal, wherein a triggering event and signal are configured to break said seal allowing said two or more reagents to mix within said bladder allowing said bladder to inflate.

19. A system for preventing a drowning incident comprising the garment of claim 1 in communication with an external processing and communication device, wherein said external processor and communication device is provided to communicate an alarm state signal based on the drowning probability score to a third party.

20. The garment of claim 1 provided in the form of a diving garment selected from diving vest, diving vest, diving buoyancy vest; wherein at least one inflatable bladder is configured to be aligned with the user's diaphragm.

* * * * *